(12) United States Patent
Wijay et al.

(10) Patent No.: US 9,592,148 B2
(45) Date of Patent: Mar. 14, 2017

(54) ACUTE AND PERMANENT OCCLUSION DEVICE, DELIVERY CATHETER AND METHOD

(76) Inventors: Nandhika Wijay, Friendswood, TX (US); Bandula Wijay, Friendswood, TX (US)

( * ) Notice: Subject to any disclaimer, the term of this patent is extended or adjusted under 35 U.S.C. 154(b) by 384 days.

(21) Appl. No.: 13/478,880

(22) Filed: May 23, 2012

(65) Prior Publication Data

US 2013/0312761 A1 Nov. 28, 2013

(51) Int. Cl.
*A61F 6/22* (2006.01)

(52) U.S. Cl.
CPC ..................... *A61F 6/225* (2013.01)

(58) Field of Classification Search
USPC .......... 128/831–841; 606/27, 28, 42, 43, 48, 606/135; 600/30, 33, 29; 607/138; 604/244
See application file for complete search history.

(56) References Cited

U.S. PATENT DOCUMENTS

| | | | | |
|---|---|---|---|---|
| 3,675,642 A * | 7/1972 | Lord | ............................. | 606/197 |
| 4,677,967 A * | 7/1987 | Zartman | ............ | A61B 10/0012 128/830 |
| 4,733,665 A * | 3/1988 | Palmaz | ......................... | 606/108 |
| 5,334,137 A * | 8/1994 | Freeman | .......... | A61B 17/12022 604/244 |
| 5,601,600 A | 2/1997 | Ton | | |
| 5,656,036 A * | 8/1997 | Palmaz | ............ | A61B 17/12022 606/158 |
| 5,746,769 A | 5/1998 | Ton et al. | | |
| 5,935,137 A * | 8/1999 | Saadat et al. | .................. | 606/135 |
| 6,357,443 B1 * | 3/2002 | Loy | .......................... | A61F 6/225 128/830 |
| 6,588,429 B1 * | 7/2003 | Wildemeersch | ............... | 128/830 |
| 6,629,533 B1 * | 10/2003 | Webb | ............... | A61B 17/12022 128/887 |
| 7,736,326 B2 * | 6/2010 | Fouere | ................ | A61F 9/00772 128/887 |
| 7,819,880 B2 * | 10/2010 | Zannis | .................. | A61F 2/4618 606/86 A |
| 7,846,160 B2 | 12/2010 | Payne et al. | | |
| 2003/0066533 A1 * | 4/2003 | Loy | .................. | A61B 17/12099 128/831 |
| 2010/0163054 A1 * | 7/2010 | Breznel et al. | ............... | 128/831 |
| 2011/0174312 A1 * | 7/2011 | Everingham et al. | ........ | 128/831 |
| 2011/0284009 A1 * | 11/2011 | Swann et al. | ................. | 128/831 |

* cited by examiner

*Primary Examiner* — Ophelia A Hawthorne
(74) *Attorney, Agent, or Firm* — Steve Rosenblatt

(57) ABSTRACT

An endoluminal occluding device consisting of a conical-shaped structure which is attached to a threaded central tubular element is capable of occluding a body lumen immediately after placement. When deployed within a body lumen, such as a fallopian tube, the conical-shaped structure extends radially outward from the central tubular element, thereby acutely occluding the body lumen, and, in the case of the fallopian tubes, preventing conception. As the acute occlusion device is being implanted into a body lumen, it is rotated, as the screw threads, which embed into the body lumen wall, advance the device within the body lumen to the desired located. Once implanted and deployed into a body lumen, the acute occlusion device provides immediate occlusion of the body lumen. A proximal anchor prevents the endoluminal device from migrating into the body lumen once it has been deployed.

20 Claims, 9 Drawing Sheets

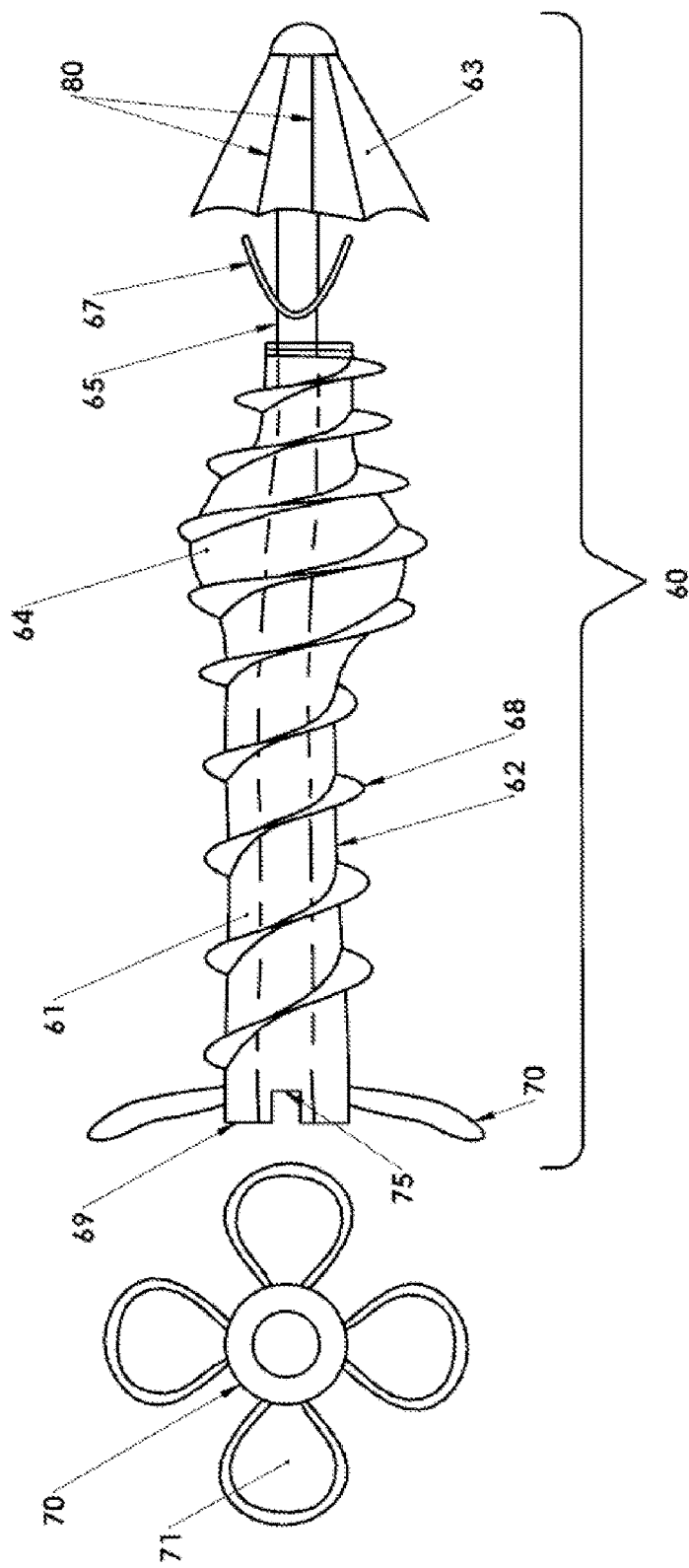

ACUTE AND PERMANENT OCCLUSION DEVICE, DELIVERY CATHETER AND METHOD

FIELD OF THE INVENTION

The present invention relates to an endoluminal occluding device, which when implanted within the fallopian tubes, facilitates female sterilization.

BACKGROUND OF THE INVENTION

Female sterilization is a very common practice and is performed frequently throughout the world. Traditionally, the most common female sterilization method is fallopian tube ligation, a procedure that utilizes a trans-abdominal approach for the occlusion, or tying, of the fallopian tubes. Despite its worldwide use, tubal ligation via the trans-abdominal approach is associated with substantial trauma, discomfort, hospital stays, and complications, such as bleeding, infection, reactions to general anesthetic, and bowel perforation. The trans-abdominal approach involves surgery, is difficult to reverse, and is not readily available to many women throughout the world. Even though local anesthetic is considered an option for the trans-abdominal approach to tubal ligation, almost all of these sterilization procedures are performed under general or spinal anesthesia. In addition, the trans-abdominal approach to tubal ligation requires incisions that invade the peritoneal cavity, thereby raising the risk of injury to intra-abdominal structures.

In order to avoid the problems associated with trans-abdominal tubal ligation procedures, various trans-cervical approaches to tubal sterilization have been proposed. The trans-cervical approach to sterilization involves the insertion of a catheter or sterilization device directly into the fallopian tubes via the reproductive tract, eliminating the need for general anesthetic and abdominal incisions. Initial trans-cervical approaches to tubal sterilization involved radiofrequency, chemical or heat induced scarring, or liquid silicone injections. However, these approaches have all failed due to safety and efficacy concerns. Chemical scarring agents, such as quinacrine, iodine, and methylcyanoacrylate, require repeated applications and have problems concerning biocompatibility. Thermal blocking procedures, which induce the formation of scar tissue within the fallopian tubes, have high failure rates and major complications such as uterine bleeding and bowel perforation. Electrocautery methods, which employ an electric current to induce scar tissue within the fallopian tubes, are also unsatisfactory because they do nor scar a sufficient amount of tissue and because they can burn surrounding organs, particularly the bowel.

Current trans-cervical methods involve occluding the fallopian tubes by implanting a small occluding device. The occluding devices in the prior art are usually in the form of a cylindrical plug or a coil. For instance, Loy in U.S. Pat. No. 6,357,443 describes a removable fallopian tube plug consisting of a tubular (cylindrical) elongate member with a number of fingerlike protrusions that extend radially outwards creating a barrier and thereby occluding the fallopian tubes. Additionally, Saadat et al. in U.S. Pat. No. 5,935,137 describe a fallopian tube occluding device for female sterilization which is a plastic, rubber, or metal elongate hollow tubular (cylindrical) structure with ribs that are either coated with copper or are interlaced with copper rings. The hollow portion of this device has a valve, or seals with a hydrogel, after the device is implanted into the fallopian tubes.

Coils, which have a helical outer surface and which assume a bent shape when released from the delivery catheter system, are also used to occlude the fallopian tubes. For example, Ton et al. in U.S. Pat. Nos. 5,601,600 and 5,746,769 describe the use of a coil to occlude the fallopian tubes. The device consists of polyethylene terephthalate (PET) fibers wrapped around a stainless steel core that is surrounded by 24 or more coils of nickel-titanium alloy. After the device is deployed within the fallopian tubes, the PET fibers induce the tubal epithelium to undergo fibrosis, which results in tubal occlusion. The device also relaxes to its natural bent shape once it is deployed in the fallopian tube. The tubal occlusion process from these devices takes about three months to complete and must be confirmed via a hysterosalpingogram.

U.S. Pat. No. 7,846,160 teaches the use of an exterior thread to advance a lumen plug by rotation In FIG. 3. In FIG. 4 barbs are held under a sheath such that when the sheath is retracted, the barbs spring out and point proximally to prevent removal.

Most of these devices eventually become dislodged or have found to be only moderately effective in preventing pregnancy. In addition, all of the fallopian tube occluding devices are either composed of metal or have metal components. As a result, various surgical procedures involving electrosurgery, radiofrequency, or microwave energy cannot be performed near the implants. Therefore, a need exists for a female contraceptive device that does not contain any metal, does not migrate once implanted, and which provides immediate protection against conception. The occlusion device of the present invention fulfills these needs.

SUMMARY OF THE INVENTION

The present invention consists of an implantable device and method for immediate and permanent occlusion of a body lumen, such as the fallopian tubes of the human female. The implant, an acute occlusion device, or lumen occluding assembly, consists of a central tube, or hollow body, which is closed at its distal end, and which carries a movable occluding device, a conical-shaped structure that functions as an occlusion means, and that is located near the distal end of the central tube. The distal end of the hollow body is resilient and can be extended remotely. The proximal body portion of the central tube, hollow body, of the implant has a screw thread which embeds into the inner lumen of a body lumen wall, and which is utilized to advance, and to seal, the implant into a body lumen. The screw thread section of the hollow body may include a portion with a larger radial dimension. Also attached to the central tube, and placed near the proximal end of the central tube, is a travel stop, or collar, which prevents the implant from migrating into the body lumen after it has been deployed. The central tube is hollow so that a push rod can be inserted into the implant. The proximal end of the implant contains an attachment means that allows the implant to be attached to a delivery catheter during the delivery, and implantation, of the device. Prior to deployment, the conical-shaped structure, which contains a series of radially-oriented struts for strength and support, is folded and held in place by a retainer, or cap, that is appropriately located on the distal portion of the central tube. The radially-oriented struts are made from a shape memory allow, which enables the conical-shaped structure to return to its natural configuration once it is released from the retainer (cap). By activating the push rod, the resilient distal end of the hollow tube extends, displacing the cap holding (or trapping) the open end of the conical-shaped structure, thereby releasing, and opening, the conical-shaped structure.

The implant is first affixed, via a pin and slot connection or similar method, onto a delivery catheter, which is a co-axial assembly having a push rod at the core that is inside a braided tube, both of which are attached to a handle. A section of the push rod extends past the distal end of the braided tube of the delivery catheter so that it can be inserted into the central tube of the implant, as the implant is being attached to the delivery catheter. A connector, at the distal end of the braided tube of the delivery catheter, is connected to an attachment means of the implant in order to secure the implant onto the delivery catheter before deployment. The attachment means can be any that is well known in the art, such as a luer connection, a bayonet connection, or a simple screw connection. The outer co-axial braided tube is attached to a knob on the handle, which when turned, is able to turn the braided tube, as well as the implant, since it is attached to the braided tube, via the connector, during deployment.

The implant, which is located at the distal end of the braided tube of the delivery catheter, is partly inserted into the entrance of a body lumen, such as the ostium of the fallopian tube. The ostium is reached by inserting the catheter through the vagina and the cervix of the uterus. After the implant is partly inserted into a body lumen, the knob on the handle of the delivery catheter is turned, causing the braided tube, and the attached implant, to rotate. The rotation enables the implant to advance further into the body lumen as the screw threads of the central tube, which are embedded into the inner lumen of the body lumen wall, are rotated. The rotation continues until the collar, at the proximal end of the implant, presses against the wall that surrounds the opening of the body lumen. The rotation means is favored over devices that are simply pushed into the fallopian tubes, as the rotation does not cause axial stress on the fallopian tube, which can often lead to complications in the procedure.

Once the implant is positioned within a body lumen, a thumb piece on the delivery catheter handle is squeezed, which causes the push rod to move distally within the braided tube and push against the closed distal end of the central tube of the implant, pushing the cap holding the folded conical-shaped structure, and causing the distal portion of the central tube of the implant to elongate, or stretch, thereby releasing the folded conical-shaped structure from the cap, and returning the conical-shaped structure to its natural, expanded form. After the conical-shaped structure has been expanded, the connector on the braided tube of the delivery device is released from the attachment means on the implant so that the delivery catheter can be withdrawn.

The implant in the present invention can be made of polymeric materials such as silicone, polyurethane, nylon, polyethylene, high density polyethylene or polypropylene, PET, or a combination thereof, or similar material, or biologically derived material, such as a patient's own tissue, or tissue made from stem cells in the form of the above described device. The delivery catheter handle can be made of rigid plastic materials such as ABS or nylon. The braids of the braided tube can be made from nylon with stainless steel wire braiding. The push rod can be made from stainless steel having a round, rectangular, or hexagonal cross section.

The principal behind the present invention is to provide a means for complete and immediate closure of a body lumen, such as the fallopian tube, eliminating the delay required for tissue growth as a means for occlusion. Immediate closure of a body lumen is achieved via a conical-shaped structure that, when opened into its natural shape, occludes the body lumen by exerting radial pressure on the body lumen's inner wall. The radial force is sufficient enough to generate a hermetic seal. The outer edge of the conical-shaped structure is serrated which enhances the embedment of the outer edge of the conical-shaped structure to the inner wall of the body lumen. The serrations are meant to "cut into" the inner wall of the occluded body lumen. The conical-shaped structure has several struts, which add strength and rigidity, as well as the radial force needed for keeping the conical-shaped structure in the open position, thereby sealing the structure against the inner wall of the body lumen. Additionally, during deployment, the struts make the conical-shaped structure easier to fold against the central tube, where the sheath portions between the struts fold preferentially during folding. The struts may also contain memory alloys which provide additional radial force, structure, and sealing capabilities of the conical-shaped structure as it presses against the inner wall of the body lumen. The screw threads of the central tubular element, which are used to advance the implant into a body lumen as the outer braided tube of the delivery catheter is rotated, embed into the inner luminal wall of the body lumen, providing an additional measure of occlusion. Additionally, the central tubular element can include a section within the proximal region that has a larger diameter, providing yet another measure of occlusion to the device. This larger diameter portion will also help prevent the distal and proximal migration of the implanted device.

The device disclosed herein can be used for immediate occlusion of any type of body lumen, especially the fallopian tubes, wherein the device is used to achieve female sterilization. In order to enable complete sterilization, one implant of the present invention is used to occlude each of the fallopian tubes. Several variations of the present inventions are possible. For example, the conical-shaped structure can be placed on the central tube of the implant so that it opens to away from the proximal end of the implanted device or open towards the proximal end of the implanted device. The struts on the conical-shaped structure can be made from shape memory alloy in order to provide sufficient spring action so as to form a seal against the luminal wall of the body lumen. The central tube can be smooth or can be corrugated, the corrugation providing enhanced flexibility and conformity of the device within a body lumen, such as the fallopian tube. The collar at the proximal end of the device can be made as one circular collar, or can be made as several segments, or lobes, or with shape memory alloys embedded in them, so that the collars will immediately bow outwards once the device is properly positioned via the delivery catheter.

BRIEF DESCRIPTION OF THE DRAWINGS

FIG. 6 provides another embodiment of the acute occlusion device.

DETAILED DESCRIPTION OF THE PREFERRED EMBODIMENT

Figure 1:
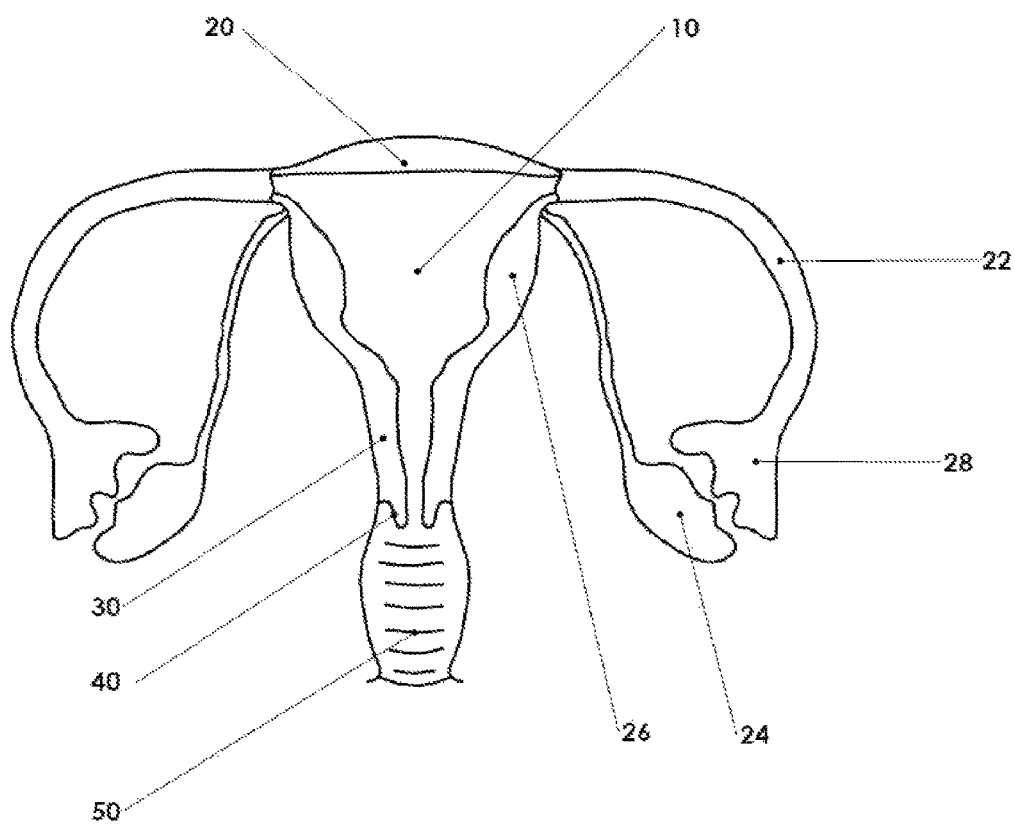
FIG. 1 is a depiction of the human female reproductive system.

FIG. 1 is a diagram of the human female reproductive system. Prior to conception, the ovum, which originates in the ovary (24), enters the fimbriae (28), migrates through the fallopian tube (22), and enters the uterus (10) just below the fundus uterus (20). The endometrium (26) is the inner lining of the uterus (10) and the myometrium (30) is just above the cervix (40) which in turn is just above the vagina (50).

Figure 2:
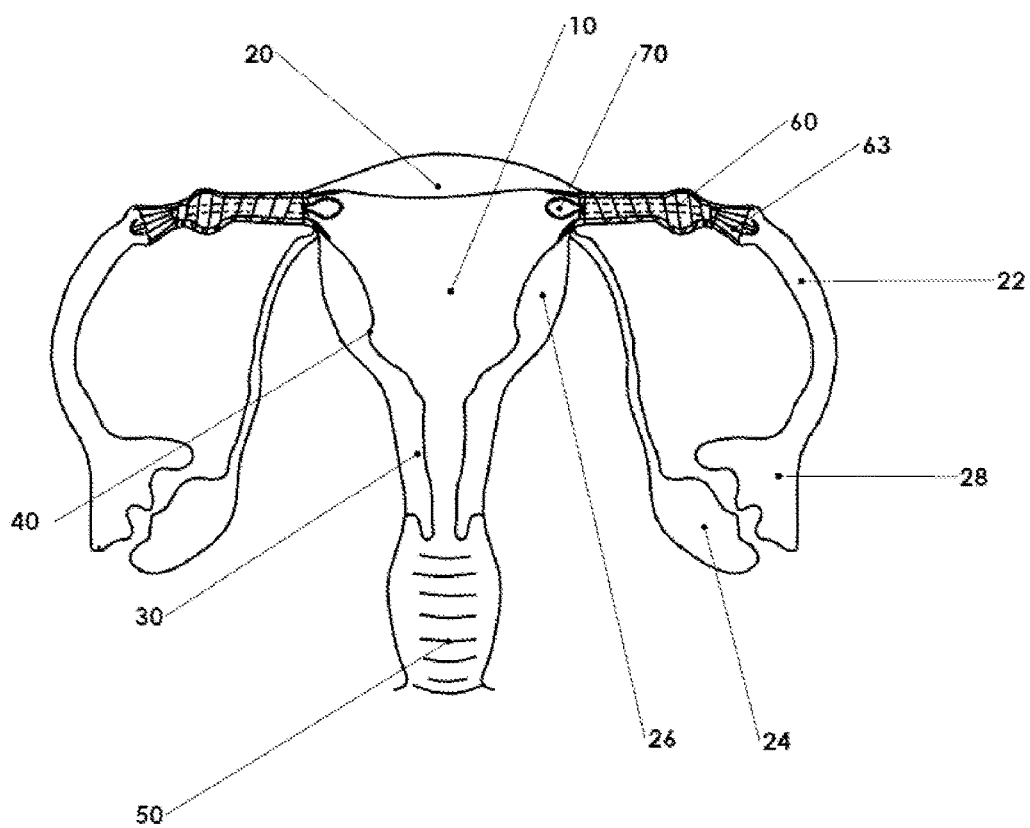
FIG. 2 shows the acute occlusion device of the present invention after it has been deployed within the fallopian tubes.

FIG. 2 shows the acute occlusion device, or lumen occluding assembly (60), of the present invention when it is deployed in the fallopian tubes (22) of the human female, via a delivery catheter (100 in FIG. 4), the acute occlusion device (60) is placed within a body lumen, such as a fallopian tube (22). A travel stop, or collar (70), is attached to the proximal end of the acute occlusion device (60) to prevent the migration of the device (60) into the body lumen, such as a fallopian tube (22). The acute occlusion device (60) includes a conical-shaped structure, or movable occluding device (63), which when deployed in a body lumen, such as a fallopian tube (22), by release of potential energy retained therein, opens into its natural form and presses against the inner wall of a body lumen, thereby occluding the body lumen and preventing the passage of any material or substance across it.

Figure 3A:
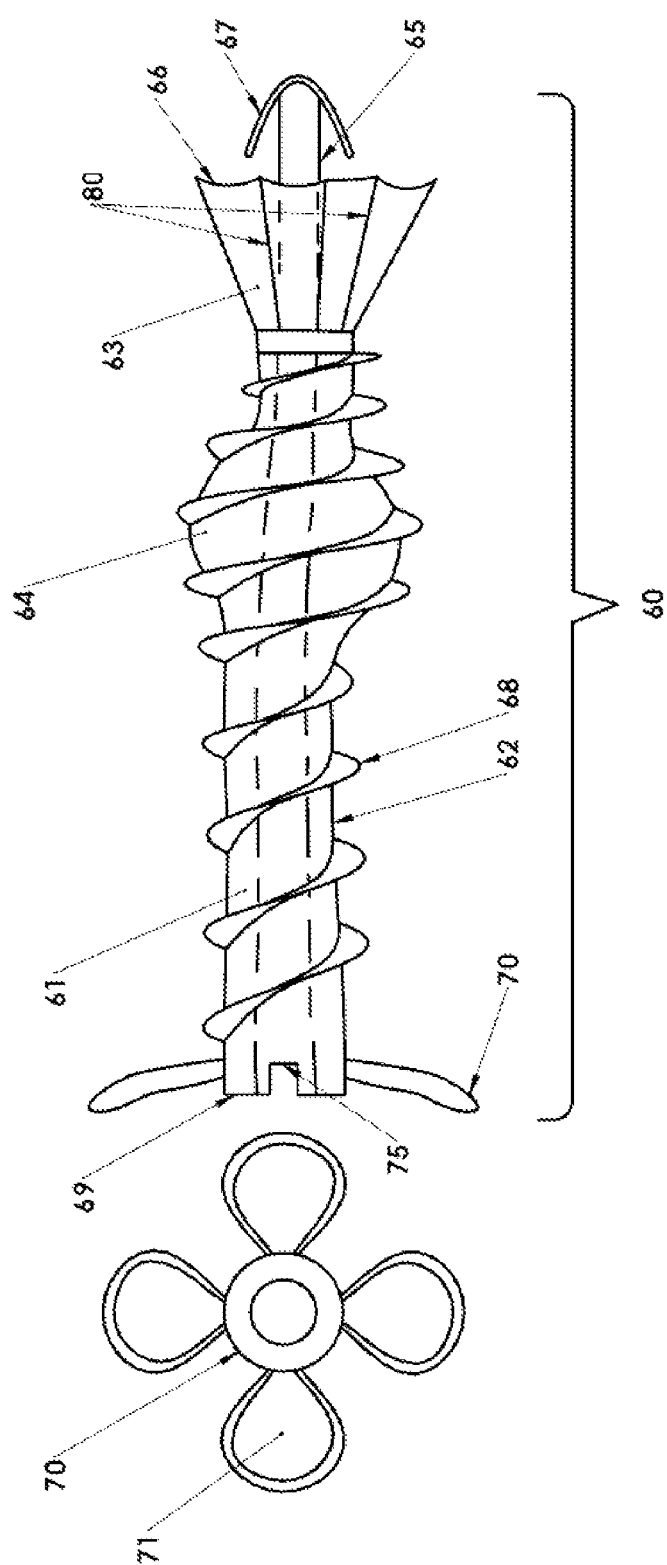
FIG. 3A is a view of the acute occlusion device, in its deployed, or natural, configuration.

FIG. 3A shows the acute occlusion device (60) of the present invention after it has been implanted and deployed within a body lumen. The acute occlusion device (60) consists of a central tubular element, or hollow body (61), composed of polyethylene, polyurethane, polypropylene, high density polyethylene, nylon, or silicone, or biologically made material that has two main sections, a proximal section (62) which may contain a portion (64) with an increased diameter, and a resilient distal section (65). The proximal section (62) of the central tubular element (61) of the acute occluding device (60) has optional screw threads or a helix having a constant or variable pitch (68) which extends along all, or a portion, of its length. The travel stop, or collar (70), is attached at the proximal end (69) of the proximal section (62) of the central tubular element (61), and can have a disk shape, or can be composed of two or more lobes (71). The proximal end (69) of the proximal section (62) of the central tubular element (61) also has an attachment means (75) which is used to attach the acute occlusion device (60) to the delivery catheter (100 in FIG. 4). The distal section (65) of the central tubular element (61) contains an occluding member, or conical-shaped structure (63), which is attached at the proximal end of the distal section (65). This conical-shaped structure (63) has struts (80), which add strength and rigidity, while the conical-shaped structure at its open end has a serrated edge (66). In its natural, unhindered, and deployed state, the conical-shaped structure (63) resembles a cone with the serrated edge extending radially outward from its point of attachment along the central tubular element (61). The distal section (65) of the central tubular element (61) also has a retainer, or cap (67), which keeps the conical-shaped structure (63) folded against the distal section (65) of the central tubular element (61) while the acute occlusion device (60) is being placed within a body lumen, such as the fallopian tube (22). A push rod (120 in FIG. 4) is used to extend the distal section (65) of the central tubular element (61) which shifts the cap (67) axially forward, thereby releasing the conical-shaped structure (63) of the acute occlusion device (60), enabling it to open into its natural, unfolded configuration so that the serrated edge (66) of the conical-shaped structure (63) presses against the inner wall of a body lumen, such as the fallopian tube (22 in FIG. 2).

Figure 3B:
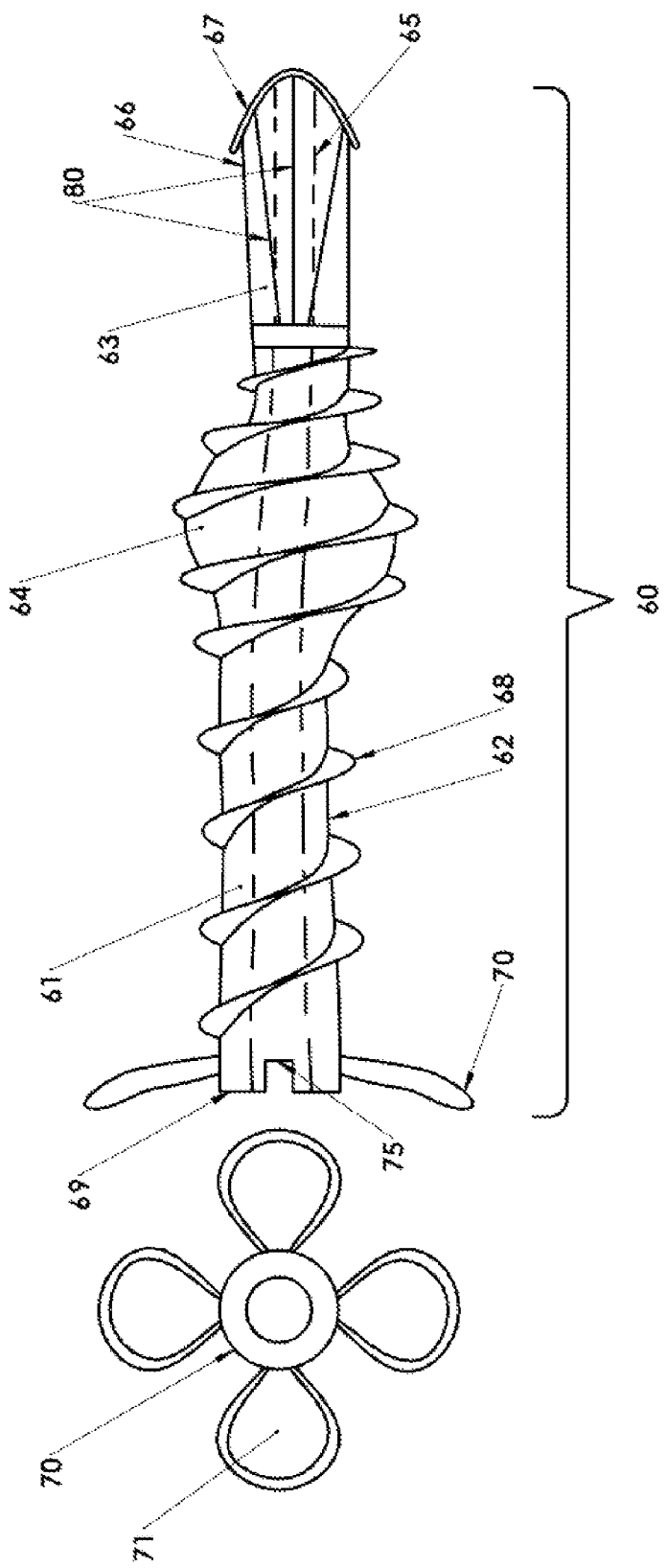
FIG. 3B is a view of the acute occlusion device in its non-deployed, or folded, configuration.

FIG. 3B shows the acute occlusion device (60) in its non-deployed configuration, prior to implantation. In this configuration, the conical-shaped structure (63) is folded against the central tubular element (61) thereby minimizing its cross sectional profile, so that the acute occlusion device (60) can be inserted into a body lumen, including narrow vessels, such as the fallopian tubes (22 in FIG. 1).

Figure 4:
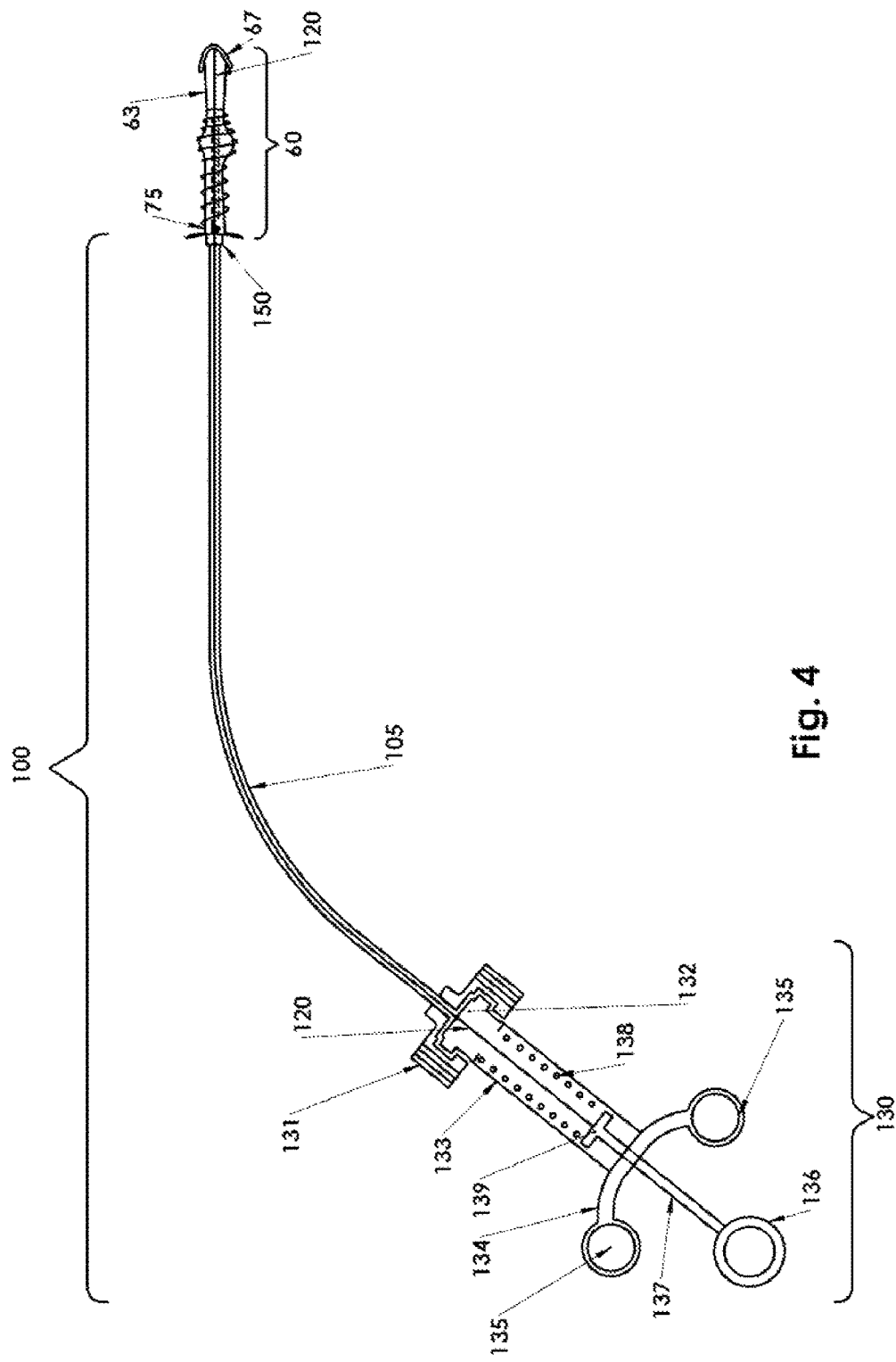
FIG. 4 shows the delivery catheter for the acute occlusion device.

FIG. 4 shows the acute occlusion device (60) attached to the delivery catheter (100). The delivery catheter (100) consists of a braided tube (105), which is capable of torque, a handle (130), and a push rod (120) which resides within the braided tube (105), and which extends from the handle (130) to a few inches past the distal end of the braided tube (105). A connector (150), located at the distal end of the braided tube (105), attaches the acute occlusion device (60) to the delivery catheter (100) when it is inserted into the attachment means (75) of the acute occlusion device (60), and after the distal end of the push rod (120) has been inserted into the entire length of the central tubular element (61) of the acute occlusion device (60). The handle (130) which is located at the proximal end of the delivery catheter (100), is attached to the proximal end of the braided tube (105). The braided tube (105) is attached to the knob (131) of the handle (130), which can rotate around the distal head (132) of the handle shaft (133). When the knob (131) is turned, the braided tube (105) rotates, which rotates the acute occlusion device (60) as it is being inserted into a body lumen. The handle (130) also has a finger piece (134), with two finger holes (135), and a thumb ring (136), which is attached to a piston rod (137) that extends through the finger piece (134). The piston head (139), located within the handle shaft (133), is held in position against the finger piece (134) via a spring (138) that is also contained within the handle shaft (133). When the finger piece (134) and thumb ring (136) are squeezed together, the piston head (139) compresses the spring (138) within the handle shaft (133) and moves the push rod (120) distally through the braided tube (105), forcing the extension of the distal section (65) of the acute occlusion device (60), which causes the cap (67) at the distal end of the acute occlusion device (60) to shift axially, thereby releasing the conical-shaped structure (63) from the cap (67).

Figure 5:
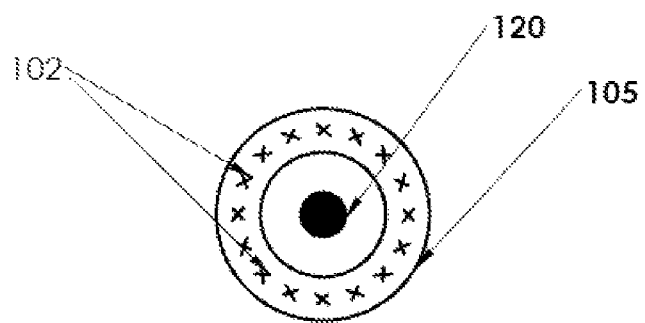
FIG. 5 is a cross section of the delivery catheter.

FIG. 5 is a cross section of the braided tube (105) of the delivery catheter (100). The braids (102) of the braided tube (105) give the braided tube (105) the strength necessary to enable torque so that the braided tube (105) can rotate along its length, thereby rotating the attached acute occlusion device (60) as it is being inserted into a body lumen. The braids (102) of the braided tube (105) are encased in plastic.

FIG. 6 provides another embodiment of the acute occlusion device (60). In this embodiment, the positions of the conical-shaped structure (63) and cap (67) are reversed, with the conical-shaped structure (63) attached at the far distal end of the distal section (65) of the central tubular element (61), and the cap (67) attached to the distal end of the proximal section (62) of the central tubular element (61). The cap (67) is positioned facing the distal end of the device, thereby overlapping the serrated edge (66) of the conical-shaped structure (63) and keeping it folded against the central tubular element (61) as the acute occlusion device (60) is being inserted into a body lumen. In this embodiment, when the push rod (120) is advanced via the handle (130) of the delivery catheter (100), the conical-shaped structure (63), since it is attached to the distal section (65) of the central tubular element (61), shifts distally, and axially, so that the serrated edge (66) is released from the cap (67), thereby releasing the conical-shaped structure (63) so that it opens to its natural configuration and faces toward the proximal end of the acute occlusion device (60).

Figures 7A, 7B:
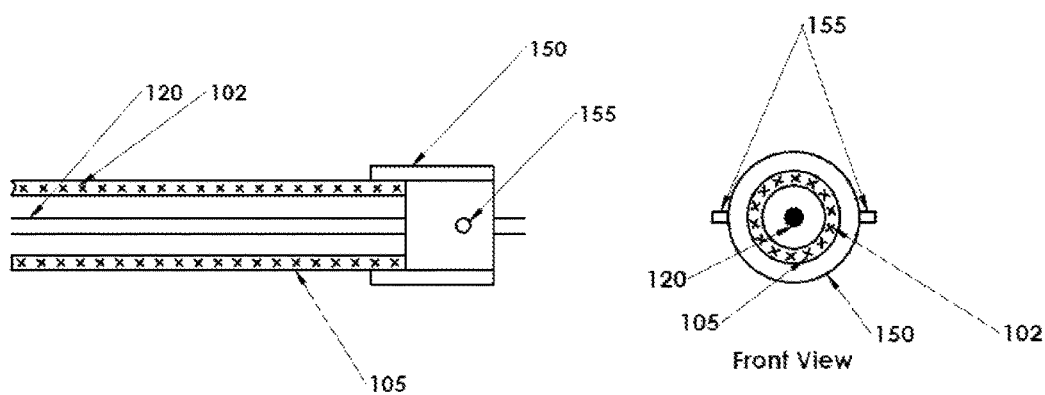
FIG. 7A is magnified view of the connector at the distal end of the delivery catheter.
FIG. 7B is the front view of the connector at the distal end of the delivery catheter.

FIG. 7A is magnified view of the connector (150) at the distal end of the braided tube (105) of the delivery catheter (100 in FIG. 4). The connector (150) is a small hollow cylindrical sleeve with two pins (155) that are positioned on opposite sides of the connector (150), and that extend a short distance from the surface. The pins (155) insert into the attachment means (75 in FIG. 3A) of the acute occlusion device (60 in FIG. 3A) with the pins (155) oriented so that they will insert into the slots (160 in FIG. 7A) of the attachment means (75 in FIG. 3A). The push rod (120) extends through the connector (150) and into the central tubular element (61 in FIG. 3A) of the acute occlusion device (60 in FIG. 3A). FIG. 7B is the front view of the connector (150) at the distal end of the delivery catheter (100 in FIG. 4). The push rod (120) extends through the connector (150) and into the acute occlusion device (60 in FIG. 3A).

Figure 8A:
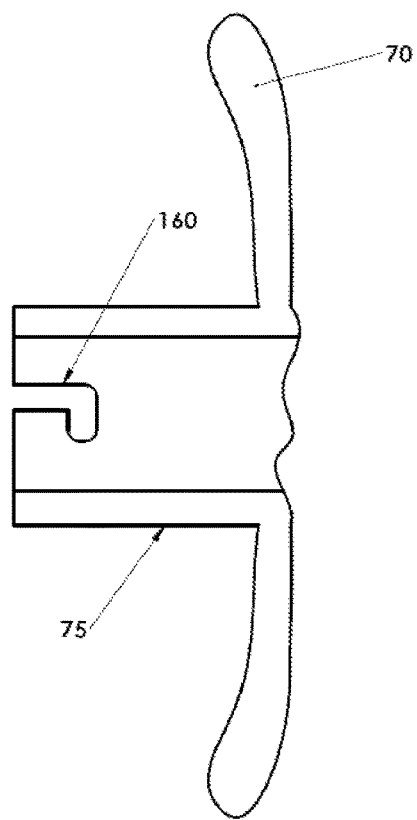
FIG. 8A is a magnified view of the attachment means of the acute occlusion device, which is used to connect the acute occlusion device to the connector of the delivery catheter.

FIG. 8A is a magnified view of the attachment means (75) of the acute occlusion device (60 in FIG. 3A), which is used to connect the acute occlusion device (60 in FIG. 3A) to the connector (150 in FIG. 7A) of the delivery catheter (100 in FIG. 4). The attachment means (75) of the acute occlusion device (60 in FIG. 3A) contains two slots (160) which are on opposite sides of the attachment means (75). The connector (150 in FIG. 7A) is inserted into the attachment means (75) of the acute occlusion device (60 in FIG. 3A). The collar (70) is attached to the proximal section (62 in FIG. 3A) of the central tubular element (61 in FIG. 3A) and is distally adjacent to attachment means (75).

Figure 8B:
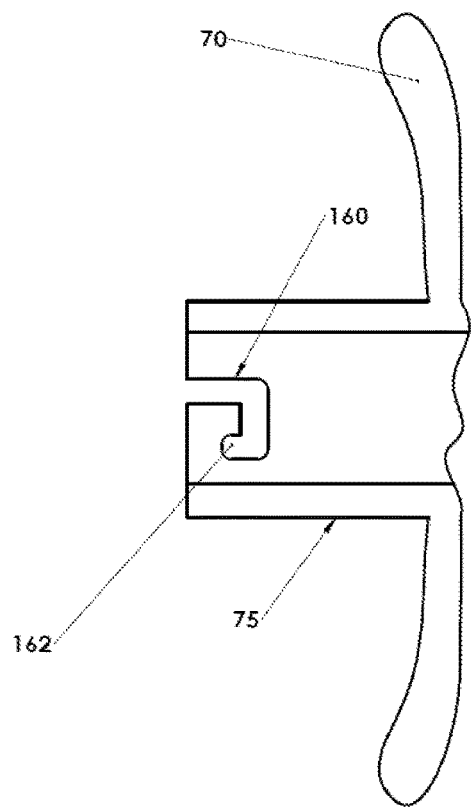
FIG. 8B provides another embodiment of the attachment means of the acute occlusion device.

FIG. 8B provides another embodiment of the attachment means (69) of the acute occlusion device (60 in FIG. 3A). In this embodiment, the slots (160) of the attachment means (69) have an extra bend (162).

We claim:

1. A female sterilization assembly comprising
a hollow body closed at one end, said hollow body remaining in the lumen for selective occluding thereof by virtue of insertion thereof;
a movable occluding device mounted to an outer surface of said hollow body and selectively remotely operated through said hollow body by elongation of said hollow body to release said occluding device to radially extend an initially circumferentially continuous edge thereof into contact with the lumen to occlude the lumen.

2. The assembly of claim 1, wherein:
said occluding device is retained with a retainer mounted to said hollow body.

3. The assembly of claim 2, wherein:
said occluding device is released by relative movement between said occluding device and said retainer.

4. The assembly of claim 3, wherein:
said relative movement is created by elongation of said hollow body.

5. The assembly of claim 4, wherein:
said elongation is initiated with a force delivered through an open proximal end of said hollow body.

6. The assembly of claim 5, wherein:
said force is delivered through a rod extending through said open proximal end of said hollow body.

7. The assembly of claim 6, further comprising:
a flexible delivery device releasably connected adjacent said open proximal end;
said delivery device comprising a tubular body through which said rod extends;
said hollow body is steered through rotation of said tubular hollow body.

8. The assembly of claim 7, wherein:
said delivery device is connected to said hollow body with a pin and slot connection where said slot has at least one bend.

9. The assembly of claim 4, wherein:
said hollow body has a resilient distal end.

10. The assembly of claim 2, wherein:
said occluding device is located on said hollow body either proximally or distally of said retainer.

11. The assembly of claim 1, wherein:
said occluding device comprises a first end secured to said hollow body and a second open end such that a generally open cone shape is defined.

12. The assembly of claim 11, wherein:
said cone shape further comprises at least one axially extending strut.

13. The assembly of claim 11, wherein:
said second end further comprises serrations for sealing contact with said lumen.

14. The assembly of claim 1, wherein:
said occluding device retains potential energy that is released for said selective occluding of the lumen.

15. The assembly of claim 14, wherein:
said occluding device is retained with a retainer mounted to said hollow body;
said occluding device is released by relative movement between said occluding device and said retainer;
said relative movement is created by elongation of said hollow body.

16. The assembly of claim 1, wherein:
said hollow body further having an intermediate larger radial dimension.

17. The assembly of claim 16, wherein:
said hollow body comprises a helix having a uniform or non-uniform pitch.

18. The assembly of claim 1, wherein:
said hollow body further comprises a travel stop adjacent a proximal end thereof and on an opposite end of said hollow body from said occluding device.

19. A lumen occluding assembly comprising
a hollow body closed at one end, said hollow body remaining in the lumen for selective occluding thereof by virtue of insertion thereof;
a movable occluding device mounted to an outer surface of said hollow body and selectively remotely operated through said hollow body such that said hollow body and said occluding device, when operated to radially extend to contact the lumen circumferentially, combine to occlude the lumen;
said occluding device comprises a first end secured to said hollow body and a second open end such that a generally open cone shape is defined;

said cone shape further comprises at least one axially extending strut;
said at least one strut comprises a plurality of circumferentially spaced struts;
said occlusion device folding between adjacent struts when retained by a retainer mounted to said hollow body.

20. The assembly of claim 19, wherein:
at least some of said struts are made of a shape memory alloy to bias said occluding device to sealingly contact the lumen when released by said retainer.

\* \* \* \* \*